United States Patent
Schrader et al.

(10) Patent No.: US 9,546,967 B2
(45) Date of Patent: Jan. 17, 2017

(54) APPARATUS AND METHOD FOR IDENTIFYING DEFECTS WITHIN THE VOLUME OF A TRANSPARENT SHEET AND USE OF THE APPARATUS

(71) Applicant: SCHOTT AG, Mainz (DE)

(72) Inventors: Bruno Schrader, Gruenenplan (DE);
Frank Macherey, Wiesbaden (DE);
Holger Wegener, Alfeld (DE); Michael Stelzl, Mainz (DE)

(73) Assignee: SCHOTT AG, Mainz (DE)

( * ) Notice: Subject to any disclaimer, the term of this patent is extended or adjusted under 35 U.S.C. 154(b) by 189 days.

(21) Appl. No.: 14/453,732

(22) Filed: Aug. 7, 2014

(65) Prior Publication Data
US 2014/0347664 A1    Nov. 27, 2014

Related U.S. Application Data

(63) Continuation of application No. PCT/EP2012/076976, filed on Dec. 27, 2012.

(30) Foreign Application Priority Data

Feb. 7, 2012 (DE) .......................... 10 2012 002 174

(51) Int. Cl.
*G01B 9/02*     (2006.01)
*G01N 21/958*   (2006.01)
(Continued)

(52) U.S. Cl.
CPC .............. *G01N 21/958* (2013.01); *G01B 9/02* (2013.01); *G01N 21/49* (2013.01); *G01N 21/896* (2013.01);
(Continued)

(58) Field of Classification Search
CPC .... G01N 21/896; G01N 21/94; G01N 21/958; G01N 2021/4709; G01N 2021/8967
See application file for complete search history.

(56) References Cited

U.S. PATENT DOCUMENTS 4,560,277 A * 12/1985 Monzer ............. G01N 21/8901
356/366
5,923,423 A *  7/1999 Sawatari ............... G01N 21/94
356/237.5

(Continued)

FOREIGN PATENT DOCUMENTS

CN      101175986 A     5/2008
EP      0850397 B1      4/2002

(Continued)

OTHER PUBLICATIONS

International Search Report dated Mar. 15, 2013 corresponding to PCT/EP2012/076976, with English translation, 7 pages.

(Continued)

*Primary Examiner* — Michael A Lyons
(74) *Attorney, Agent, or Firm* — Ohlandt, Greeley, Ruggiero & Perle, LLP (57) ABSTRACT

An apparatus for identifying defects within the volume of a transparent sheet, such as a glass sheet, is provided. The apparatus includes an illumination device that directs incident light onto at least a portion of a surface of the sheet so as to illuminate the sheet, and an image detector onto which the light backscattered from the sheet is directed to image the sheet. The apparatus generates at least two interference images under different capturing conditions in order to perform identification of defects by evaluating the at least two interference images.

20 Claims, 6 Drawing Sheets

(51) Int. Cl.
  *G01N 21/896* (2006.01)
  *G01N 21/49* (2006.01)
  *G01N 21/45* (2006.01)
  *G01N 21/94* (2006.01)
  *G01N 21/47* (2006.01)

(52) U.S. Cl.
  CPC .............. *G01N 21/45* (2013.01); *G01N 21/94* (2013.01); *G01N 2021/4709* (2013.01); *G01N 2021/8967* (2013.01)

(56) References Cited

U.S. PATENT DOCUMENTS

| | | | |
|---|---|---|---|
| 6,806,959 B2* | 10/2004 | Tukker | G01N 21/95 356/484 |
| 7,196,800 B1 | 3/2007 | Birdsley et al. | |
| 7,671,978 B2* | 3/2010 | Clark | G01N 21/4738 356/237.1 |
| 2002/0154814 A1 | 10/2002 | Gerhard et al. | |
| 2003/0053076 A1 | 3/2003 | Adachi | |
| 2005/0018199 A1* | 1/2005 | LeBlanc | G01N 21/958 356/477 |
| 2005/0078319 A1 | 4/2005 | De Groot | |
| 2011/0058160 A1* | 3/2011 | Tan | G01N 21/896 356/237.2 |
| 2011/0304854 A1 | 12/2011 | Li | |
| 2012/0019834 A1* | 1/2012 | Bornhop | G01N 21/45 356/517 |
| 2012/0133952 A1* | 5/2012 | Lee | G01B 11/306 356/600 |

FOREIGN PATENT DOCUMENTS

| | | |
|---|---|---|
| JP | 2005512075 A | 4/2005 |
| JP | 2007057521 | 3/2007 |
| JP | 2010107355 | 5/2010 |
| JP | 4576962 B2 | 11/2010 |
| KR | 20070121820 | 12/2007 |
| WO | 9710487 A1 | 3/1997 |
| WO | 03050470 A2 | 6/2003 |
| WO | 2004079406 A2 | 9/2004 |
| WO | 2006108137 A2 | 10/2006 |

OTHER PUBLICATIONS

German Office Action dated Oct. 25, 2012 corresponding to German Application No. 10 2012 002 174.7 with English translation, 8 pages.

First Written Opinion of the International Searching Authority dated Mar. 15, 2013 corresponding to PCT/EP2012/076976, 5 pages.

Second Written Opinion of the International Searching Authority dated Mar. 24, 2014 corresponding to PCT/EP2012/076976, 5 pages.

English translation of the International Preliminary Report on Patentability dated May 15, 2014 corresponding to PCT/EP2012/076976, 6 pages.

* cited by examiner

APPARATUS AND METHOD FOR IDENTIFYING DEFECTS WITHIN THE VOLUME OF A TRANSPARENT SHEET AND USE OF THE APPARATUS

CROSS REFERENCE TO RELATED APPLICATIONS

This application is a continuation of International Application Serial No. PCT/EP2012/076976 filed Dec. 27, 2012, which claims benefit under 35 U.S.C. §119(a) of German Patent Application No. 10 2012 002 174.7, filed Feb. 7, 2012, the entire contents of both of which are incorporated herein by reference.

BACKGROUND

1. Field of the Disclosure

The invention generally relates to quality control in the manufacturing and/or processing of a transparent sheet, preferably a glass sheet, and more particularly relates to the identification of imperfections or defects within the volume of the sheet.

2. Description of Related Art

In glass manufacturing, defect inspection is usually implemented by optical imaging methods. That is, defects in the material of a test object are imaged on a CCD chip by illuminating the test object, for example based on a bright field or dark field method, and using a lens system. The image so generated is evaluated in a computer unit, and based on the image information it is decided whether there is a defect in the glass, and optionally what kind of glass defect. Defect sensitivity of such systems depends on the pixel resolution, the resolution of the objective lens, and the signal-to-noise ratio of the recording unit.

The data rates of the image sensors which are typically implemented in form of line scan cameras are limited. A line scan camera having a horizontal frequency from 25 to 50 kHz, for example, can be employed with a feeding rate of the test object from 15 to 30 m/min. Usually one illumination channel is used. When using a plurality of channels, a plurality of camera benches would be needed accordingly.

An increase of the feeding rate of the production line would mean that with unaltered illumination less light would be available per image line, so that the signal-to-noise ratio would decrease. Alternatively, in order to avoid such deterioration, pixel resolution in the feeding direction could be reduced. This, however, would reduce the defect sensitivity.

In optical imaging systems, an increase in optical resolution causes a reduction in the depth of field, which should at least correspond to the glass thickness of the test object to be examined. Usually, even greater depths of field are required, due to feeding tolerances and because of a possible deflection of the glass.

Thus, for resolutions of less than 20 μm per pixel and feeding rates of 35 meters per minute, for example, imaging systems would become complex, difficult to control, and expensive.

Approaches for inspecting the skin or the volume of objects for defects are known in the prior art.

JP 4576962 B2 discloses a method for identifying defects in test objects, for example variations in thickness of a planar film due to a foreign body. For this purpose, light is irradiated onto the test object, and the backscattered light is analyzed. The analysis is based on an analysis of the polarized components of the backscattered light.

WO 2006/108137 A2 discloses an identification of defects in a glass sheet using a system which directs the light from a laser diode onto the glass sheet to be checked and evaluates the light backscattered from the front and rear surfaces of the glass sheet onto a line scanner as an interference pattern.

A problem of the prior art methods is that the line scanners used have a sensor area of approximately the dimension of the test object. Further, due to contaminations, the measured images frequently provide patterns without the presence of any defect in the test object, so that automatic evaluation of the images may be prone to errors. Furthermore, due to the sample geometry, patterns caused by minor defects may adversely be superimposed by a primary pattern, so that the defect cannot be detected reliably.

SUMMARY

The invention is based on the object to provide for identification of defects within the volume of a transparent sheet which allows to efficiently identify defects and which can be implemented at low costs.

One aspect of the invention relates to an apparatus for identifying defects within the volume of a transparent sheet, preferably a glass sheet, wherein the sheet may be a substantially 2-dimensional rectangular object, for example. The sheet may be flat, curved, or may have any other shape. The apparatus generally permits to capture and identify defects in an outer wall or within a volume of an object.

The apparatus may comprise illumination means for illuminating the sheet. Using the illumination means, light may be directed onto a portion of a surface or to the entire surface of the sheet. The illumination means may in particular be adapted to illuminate a sheet which is moved relative to the illumination means in a feeding direction. The incident light may be incident on the sheet in form of a strip of light, with the light strip illuminating the entire width of the sheet. The width herein refers to a dimension of the sheet transversely to the feeding direction.

The incident light may be a light spot that illuminates i) a portion of, or ii) the entire sheet. In case of i), the light spot may scan the sheet transversely to the feeding direction.

The apparatus may further comprise image detection means onto which the light backscattered from the sheet is directed for imaging the sheet. Below, backscattered light refers to light which is deflected towards the image detection means when illuminating the sheet, due to an interaction of the incident light with the sheet, preferably by reflection or diffraction at the sheet. The image detection means may be adapted to generate at least two images, preferably digital or electronic images.

The apparatus may be adapted to generate at least two interference images under different capturing conditions in order to identify the defects or to enable identification of the defects by evaluating the at least two interference images. Evaluation of the interference images may be accomplished by an operator, or optionally by a computing unit connected to the image detection means and/or to the illumination means.

An interference image refers to an image that includes an interference pattern. Advantageously, based on a plurality of interference images that were recorded under different capturing conditions it is possible to detect even small and very small defects, in addition to large and medium-sized defects.

An interference pattern may be created when incident light is reflected at an upper or outside surface and at a lower or inside surface of the sheet. The reflected or backscattered light therefore will have two components which superimpose. The superposition of the reflected light components may therefore produce an interference pattern at the location of the image detection means.

The visible effect of a defect, however, is not caused so much by the scattering or refraction on an imperfection or defect of the sheet as rather by the local disorder of the matrix material of the sheet caused by the defect. The defect pattern is therefore a result of a deformation of a wavefront due to the local disorder in the material and superposition thereof with an undisturbed wavefront of a reference wave.

According to one embodiment, the apparatus for identifying defects may be adapted to enable or to perform identification of the defects by a comparison of the interference images. Identification of the defects may be accomplished by the operator or, optionally, by the computing unit.

The comparison of the interference images may preferably include to determine differences between the interference images. For this purpose, interference images may be used which are produced sequentially in time or, optionally, at the same time.

The comparison of the interference images may also include to display the interference images on one or more screens, so that the differences between the interference images are determined by the operator.

A comparison of interference images that were generated under different capturing conditions may show, for example, that an interference pattern caused by the defect varies more quickly than the basic interference pattern of the sheet. The images will include different patterns which when combined allow for a representation that may be useful in a subsequent pattern recognition.

Advantageously, based on a comparison of a plurality of interference images that were recorded under different capturing conditions it is possible to detect even small and very small defects, in addition to large and medium-sized defects. For example, it is possible to detect solid inclusions of a core size of <50 µm and gas inclusions of a core size of <150 µm.

In a series of several interference images generated under different capturing conditions, an interference pattern in one of the interference images may be assumed as an expectation value which is used as a reference for the other interference patterns. The expectation value may be compared with the interference patterns of each of the other images.

A defect may be distinguished by the fact that the interference patterns in different images deviate from the expectation value. The deviations may be added, so that small defects can be detected and larger defects can be detected in more detail.

The comparing of interference images may be accomplished by determining a difference, by correlation, or by checking a similarity between the expectation value and the interference patterns of each of the other images.

Advantageously, dirt and stain may be discriminated in the difference images due to their consistent behavior. Furthermore, by comparing a plurality of interference images, defects may be identified that are difficult to be noticed in a single interference image because of a low intensity or amplitude of the interference waves due to an unfavorable superposition of the interference pattern of the defect with the basic pattern.

It is optionally also possible to detect a defect by identifying a disturbance in an interference image. For this purpose the interference image may for example be checked for the presence of an alteration or disturbance in the interference pattern as compared to an undisturbed interference pattern or as compared to an interference pattern in an undisturbed region of the interference image. An undisturbed interference pattern may be created due to the fact that even a volume region of the sheet which does not include any defect will cause interference. However, in the vicinity of a defect the light passes through a different path than in the undisturbed regions, so that a defect which causes an inhomogeneity of the refractive index of the sheet will lead to an alteration or disturbance of the interference pattern.

For identifying a defect, interference images have many advantages over optical images of the sheet. The disturbance caused in the interference image due to a defect is larger than the defect, e.g. by a factor of 10 or 12. Therefore, a lower optical resolution will suffice to detect a defect. In contrast to a defect in the material, dirt on the surface of an object will not cause a disturbance when comparing a plurality of interference images. This allows discrimination of a material defect from superficial dirt. Disturbances that are small in relation to the optical resolution can be identified by multiple observations and exploitation of the signal change which is larger as compared to a signal change in an undisturbed region.

Another aspect of the invention relates to a method for identifying defects within the volume of a transparent sheet, preferably a glass sheet.

The detection can be performed using illumination means for illuminating the sheet, and image detection means for capturing the light backscattered from the sheet.

Using the illumination means, incident light may be generated and directed onto at least a portion of a surface of the sheet, the illumination means preferably comprising at least one light source.

In one step of the method, the sheet may be illuminated by the illumination means so that light is scattered or backscattered by the sheet and is directed towards the image detection means.

In a further step, the backscattered light may be captured by the image detection means.

In a further step, at least two interference images may be generated by the image detection means under different capturing conditions, preferably in cooperation with the illumination means.

In a further step, the defects can be identified by evaluating the at least two interference images, for example by an operator or by a computing unit coupled to the image detection means and/or to the illumination means.

According to one embodiment, the illumination means may be adapted to generate light having at least two different wavelengths and/or waveforms. By illuminating the sheet with light of different wavelengths and capturing the light backscattered from the sheet using the image detection means, at least two interference images may be produced. On this basis, the different capturing conditions may be provided by generating a respective interference image using light of a wavelength that differs from the wavelength of the light used for generating another interference image or other interference images.

The capturing conditions of the interference images may additionally differ in that the waveforms of the light used for the respective interference images are not the same or are different.

The illumination means may preferably be adapted to direct incident light onto the sheet under at least two illumination angles. On this basis, the different capturing conditions may be provided by generating a respective interference image using incident light which is directed onto the sheet at an illumination angle which is different from the illumination angles of the incident light of further interference images.

The image detection means may in particular be adapted to capture backscattered light at different detection angles, wherein detection angle refers to that angle at which the backscattered light is incident on the image detection means. On this basis, the different capturing conditions may be provided by generating a respective interference image using backscattered light that is incident onto the image detection means at a detection angle that is different from the detection angles of further interference images.

Preferably, both the illumination angle and the detection angle of an interference image may differ from the corresponding angles of other interference images, so that the different capturing conditions can be provided in this way.

According to one embodiment, the illumination means may be adapted to generate incident light with at least two different phases, for example by generating the incident light for the respective interference images with different distances between illumination means and sheet, or by causing the entire optical path from the illumination means through the sheet to the image detection means to have different lengths for each of the interference images.

Advantageously, by using a plurality of interference images, the efficiency of evaluating the interference images for the presence of an alteration or disturbance of the interference pattern as compared to an undisturbed interference pattern can be improved. For example, the capturing conditions of the interference image may preferably be defined in a manner so as to simplify identification of an alteration or disturbance of the interference image. In particular, the identification may be simplified or improved by achieving destructive interference in the undisturbed region of the interference image.

According to one embodiment, the illumination means may include at least one light source which is provided in form of a sodium vapor lamp or a laser, for example. The light source may preferably have a coherence length greater than twice the thickness of the sheet, or greater than 3 mm.

According to another embodiment, the image detection means may comprise a screen onto which the backscattered light is directed for displaying the interference images.

The image detection means may advantageously comprise an image sensor configured as a matrix camera; a line scan camera; a line scan camera with Time Delayed Integration (TDI) sensor, which is operated as a quasi-matrix camera; or a video camera for capturing the light backscattered from the sheet onto the image sensor, or the interference images displayed on the screen. Using the matrix camera, line scan camera, or the line scan camera with TDI sensor, different detection angles may easily be realized. The image sensor is adapted for generating at least two electronic or digital interference images.

In terms of configuration, a line scan camera with TDI sensor is a matrix camera with a high aspect ratio of height to width of the sensor. Typically, the electrostatic latent image of a detector line is shifted on and added to the next detector line, so that in total the signal-to-noise ratio is improving. In one particular operation mode, such a sensor may be read out like a matrix camera, which is advantageous when inspecting a large but narrow object.

At a predefined time, the image sensor may capture the entire screen or a portion of the screen. Even when capturing a portion, the whole screen will have been captured after a detection time. The same is true for direct imaging of the sheet without using a screen.

An advantage of using a screen onto which the backscattered light is directed for visually displaying an image is that the image sensor does not need to directly capture the backscattered light. This permits to employ a smaller and less expensive image sensor.

The apparatus may advantageously comprise a computing unit coupled to the image sensor and/or to the illumination means. The computing unit is adapted to perform the evaluation of the interference images including the identification of a disturbance in the interference images and detection of a defect. Alternatively, the evaluation of the interference images may be accomplished by an operator.

Advantageously, a pattern recognition system may be operated on the computing unit for evaluating differences between the interference images and identifying a defect in the interference images. For this purpose, interference images or interference patterns are presented to the pattern recognition system in a test or learning phase, which originate from sheets that have no defect or which originate from sheets that have defects that are known. In this manner, the pattern recognition system learns to detect a disturbance or disorder in the interference images. When new interference images are presented, the so trained pattern recognition system can apply the acquired knowledge to successfully identify disturbances which are similar to the disturbances presented in the learning phase.

According to one embodiment, the apparatus may include a conveyor means which moves the sheet relative to the illumination means and/or the image detection means.

The conveyor means may advantageously comprise a roller over which the sheet is guided. In this case, the roller may be rotated by a drive to advance the sheet. Optionally, the sheet may be advanced by a drive separately from the roller.

In case of a sheet that may be made of glass and may be provided in form of a glass ribbon, for example, local warpage may arise due to internal stresses, making it difficult to define an exact position of the glass ribbon relative to the illumination means and/or the image detection means. To solve this problem, the glass ribbon may be guided over the roller, so that by bending the sheet an external tension is imposed on the sheet which compensates for internal stresses. In this manner, the position of the reflection point can be defined unambiguously.

According to a further embodiment, the illumination means may produce light with a plurality of different wavelengths sequentially in time by means of a tunable light source.

The light source may preferably be a voltage-controlled laser diode which emits light of a wavelength that depends on the applied voltage. Thus, the interference images may be generated sequentially in time, for example by causing a controller of the illumination means to provide a time varying voltage to the laser diode, and by reading out the image sensor at predefined times corresponding to specific wavelengths.

According to a further embodiment, the illumination means may produce light with a plurality of different wavelengths sequentially in time by means of a light source having a defined spectral width and a tunable filter.

The filter may preferably be a voltage-controlled filter which passes light of a wavelength that depends on the applied voltage. The range of variation of the filter approximately corresponds to the spectral width of the light source.

In this manner the interference images may be generated sequentially in time, for example by causing a controller of the illumination means to provide a time varying voltage to the filter, and by reading out the image sensor at predefined times corresponding to specific wavelengths.

According to one embodiment, the illumination means may produce light of a plurality of different wavelengths at the same or approximately the same time by using a plurality of light sources arranged in spaced apart relationship.

The illumination means may preferably comprise an array of lasers or laser diodes. Here, the wavelength of the light of a light source may be different from the wavelength of the light of any other light source. The image sensor may be adapted to provide a respective electrical signal for light of each wavelength, so that for each wavelength a separate interference image may be provided. In this manner, the interference images may be generated simultaneously or almost simultaneously.

According to one embodiment, the illumination means may preferably comprise at least 2, or 5, or 10, or 50 light sources.

Advantageously, the wavelengths differing from each other and used in generating the interference images may be defined so that destructive interference will occur in a region of the interference image undisturbed by the defect.

The simultaneous or sequential emission of light of different wavelengths and the generation of an interference image for each wavelength by the image sensor are employed to permit a selection of an optimum interference image. The optimum interference image among all interference images generated will be the image which exhibits the strongest wave cancellation or destructive interference in the undisturbed image region.

The information content of the optimum interference image in the undisturbed image region is very low because the latter has no or few image structures, so that the automatic detection or identification of a defect is much easier and more efficient in the optimum interference image.

The identification of a defect may preferably comprise producing a superposition image by a weighted superposition of interference images. The wavelengths used to generate the respective interference images in combination with a suitable choice of the weighting factors used in the weighted superposition may be defined so that destructive wave superposition occurs in a region of the interference image that is undisturbed by the defect.

The determining of appropriate wavelengths and weighting factors is an optimization process in which the wavelengths and weighting factors are varied to possibly obtain destructive wave superposition in the region of the image undisturbed by the defect. It can be achieved in this manner that the sum of the interference amplitudes is at a minimum in the region of the superposition image undisturbed by the defect, and is at a maximum in a disturbance region of the superposition image.

The sum of the interference amplitudes herein refers to a sum of the absolute values of interference amplitudes, or a sum of the squared interference amplitudes.

The superposition of the interference images may be performed pixel by pixel, preferably after the interference images have been brought in correspondence with each other by image registration.

Advantageously, the pattern recognition system permits to identify a disturbance in the superposition image with high probability of a hit.

According to another aspect, the invention relates to the use of an apparatus as described above for sorting thin glass or glass having a thickness of less than 200 µm, which has defects. Thin glass that has been checked with an apparatus according to the invention and sorted based on the test results exhibits a significantly reduced defect concentration or number of defects.

According to another aspect, the invention relates to a computer program which, when loaded into a computer or running on a computer, is capable to perform the method described above. Furthermore, the invention relates to a program storage medium or computer program product comprising such a program.

The invention will now be described in more detail by way of exemplary embodiments and with reference to the drawings. The same reference numerals therein refer to the same or equivalent elements. The features of different exemplary embodiments may be combined with each other.

DETAILED DESCRIPTION

Figure 1:
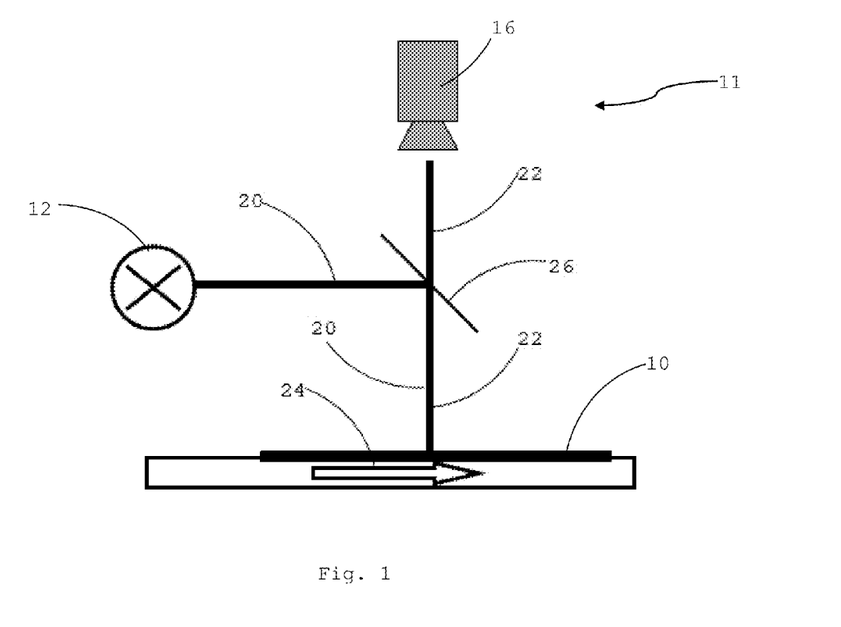
FIG. 1 is a schematic diagram of a first embodiment of the apparatus according to the invention.

FIG. 1 is a schematic diagram of a first embodiment of the apparatus 11 according to the invention. The object 10 to be inspected is a glass sheet. Apparatus 11 comprises: an illumination means 12 which directs incident light 20 onto at least a portion of a surface of sheet 10 for illuminating sheet 10; and an image detection means 16 onto which the light 22 backscattered from sheet 10 is directed for imaging sheet 10.

Apparatus 11 is adapted to generate at least two interference images at different capturing conditions. By evaluating the at least two interference images the apparatus 11 enables to identify the defects.

The defects are identified by comparing the interference images. According to the present embodiment, the comparison comprises determining the differences between the interference images. The evaluation of the interference images is performed by an operator.

The different capturing conditions are provided by generating each interference image using light of a wavelength that is different from the wavelength of the light used for generating a further interference image. In the present case, the interference images are generated simultaneously.

According to FIG. 1, the illumination means comprise a coherent light source 12 which is configured as a laser. By means of light source 12, sheet 10 is co-axially illuminated from a vertical direction. For this purpose, the light 20 emitted horizontally is deflected towards sheet 10 by a beam splitter 26. The light 22 reflected from sheet 10 passes through beam splitter 26 upwards and is captured by image sensor 16.

Beam splitter 26 exhibits selective light transmission in that the incident light 20 is reflected towards sheet 10, and the light 22 coming from sheet 10 is transmitted through the beam splitter 26.

The interference pattern is captured by a sensor line 16 having the same width as the test object. The several interference patterns are created by illumination with wavelengths $\lambda_i$ i=1, 2, . . . which are observed separated in time, or spectrally split.

The defects are identified by a comparison of the interference images, and apparatus 11 is configured to perform such a comparison. The comparison of the interference images comprises to determine differences between the interference images.

One interference image of a series of a plurality of interference images generated with different wavelengths can be used to determine an expectation interference pattern which is used as a reference for the other interference patterns. The reference pattern or expectation value is compared with the interference patterns of each of the other images by subtracting the expectation value from the respective interference pattern of the other images.

Apparatus 11 comprises a conveyor means 24 which moves the sheet 10 relative to the illumination means 12 and image detection means 16.

Figure 2:
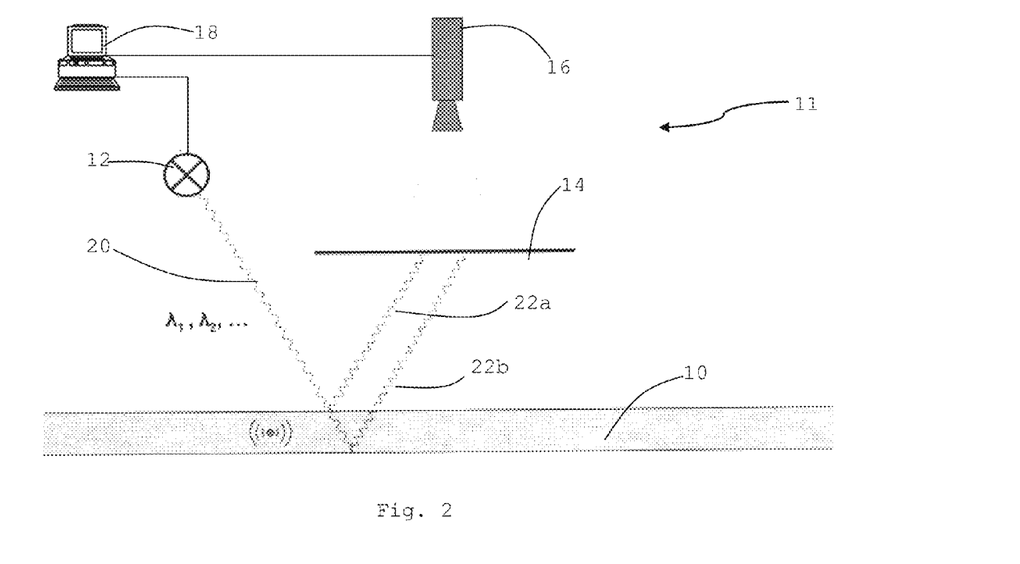
FIG. 2 is a first schematic diagram of a second embodiment of the apparatus according to the invention.
Figure 3:
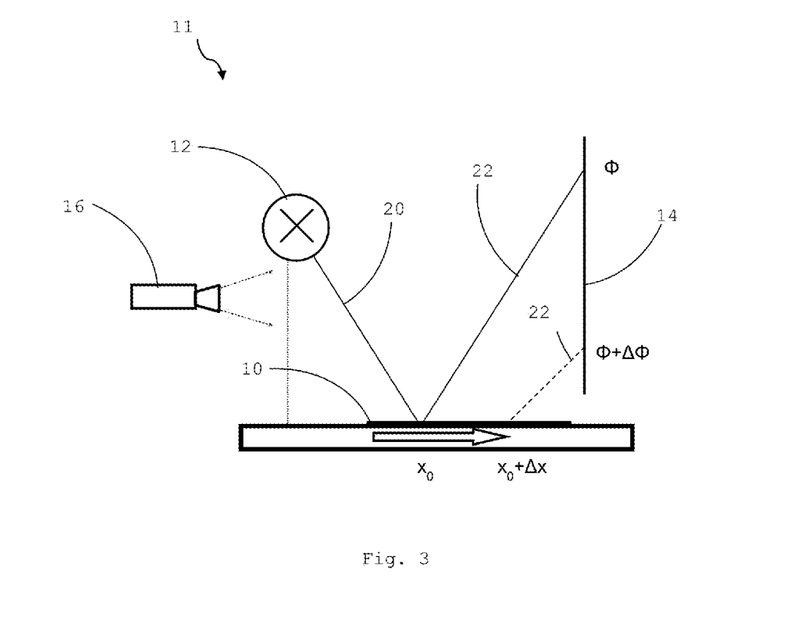
FIG. 3 is a second schematic diagram of the second embodiment of the apparatus according to the invention.

FIGS. 2 and 3 are schematic diagrams of a second embodiment of the apparatus according to the invention.

A surface area of the test object is illuminated by a coherent light source 12. The interference pattern is observed on a screen 14 and a camera/lens system 16. The image rate of the camera 16 is selected so that each point is detected a plurality of times, under different illumination angles, i.e. with different interference patterns.

A point of sheet 10, which is at a position $x_0$ at a time t (FIG. 3) will scatter the incident light 20 onto screen 14 at an illumination angle or angle of incidence which is equal to the detection angle or reflection angle ϕ of the backscattered light 22. Here, the angle of incidence and the angle of reflection ϕ are the angles of light beams 20 and 22, respectively, to the surface normal of sheet 10.

Sheet 10 is moved by conveyor means 24 in a forward direction. Consequently, at a later time t+Δt said point of sheet 10 will be located at a position $x_0$+Δx and will scatter the incident light 20 onto screen 14 at a detection angle or angle of reflection of ϕ+Δϕ. In this way, said point can be imaged on screen 14 at a plurality of illumination angles ϕ, ϕ+Δϕ, . . . , and for each angle of illumination an interference image will be generated.

Apparatus 11 comprises a computing unit 18 connected to image detection means 14, 16 and to illumination means 12. The evaluation of the interference images including the detection of a disturbance and identification of a defect is performed by means of computing unit 18.

Advantageously, by using screen 14 onto which the backscattered light 22 is directed for visualizing an image, the image sensor 16 does not need to directly capture the backscattered light 22. Thus, a smaller and cheaper image sensor 16 can be used.

An interference image is created due to the fact that incident light 20 is reflected from the upper and lower surfaces of sheet 10. The reflected light 22 therefore has two components 22a, 22b which superimpose each other. The superposition of reflected light components 22a, 22b results in an interference image at the location of image sensor 16 or screen 14. The interference pattern is generated by a variation in thickness D(x,y) of sheet 10.

$$I_{s,p}(\alpha,l,D) = R_{s,p} \times I_0 \times (1-(1-R_{s,p})e^{-i2\pi\Delta/l})^2$$

α angle of incidence to the surface normal of the sheet;
l wavelength;
D(x,y) thickness of sheet 10 at position x,y;
$I_0$ intensity;
$R_{s,p}$ Fresnel reflection coefficients with s polarization and p polarization; and
Δpath difference between the waves reflected at the upper and lower surfaces of sheet 10.

Figure 4:
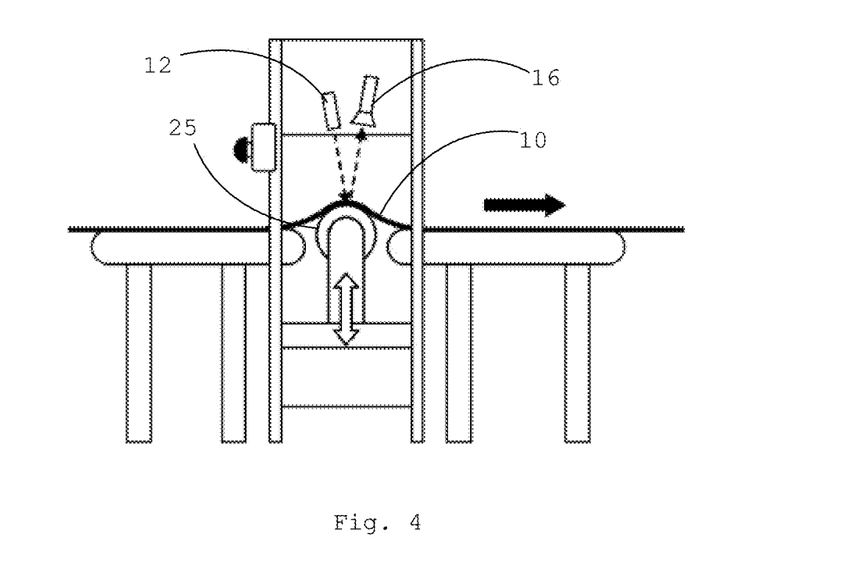
FIG. 4 is a schematic diagram of a third embodiment of the apparatus according to the invention.

FIG. 4 is a schematic diagram of a third embodiment of the apparatus 11 according to the invention. Here, the conveyor means 24 comprise a roller 25 over which sheet 10 is guided.

An observation in reflection in a reflected-light setup requires a defined position of the test object 10 (distance to image sensor 16). In case of the glass application, local warpage of the glass ribbon 10 will occur due to internal stresses, which makes a defined position even more difficult.

In order to solve this problem for observing reflection as in the interference inspection described, the glass sheet in form of a glass ribbon 10 is guided over roller 25, so that due to bending an external tension is imposed on the glass, which compensates for the internal stresses. In this manner, the position of is unambiguously defined.

Figure 5A:
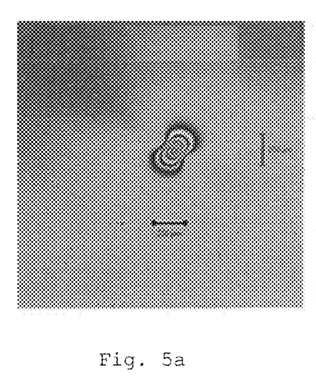
FIG. 5a is an interference image of a transparent sheet with a inclusion, at 25-fold magnification.
Figure 5B:
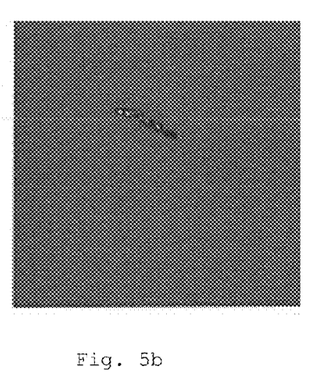
FIG. 5b is a microscopic image of the sheet used in FIG. 5a, at 100-fold magnification.
Figure 6A:
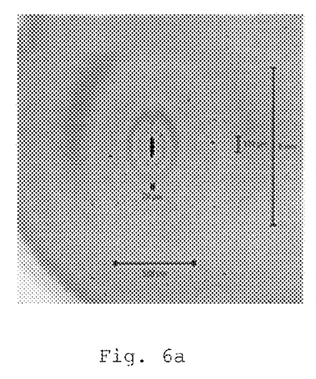
FIG. 6a is an interference image of a transparent sheet with a gas bubble, at 25-fold magnification.
Figure 6B:
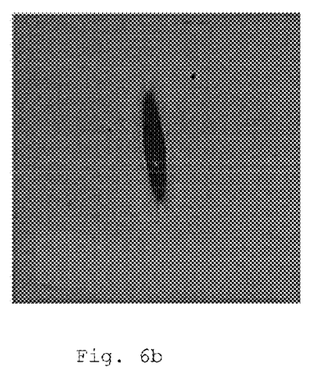
FIG. 6b is a microscopic image of the sheet used in FIG. 6a, at 100-fold magnification.
Figure 7A:
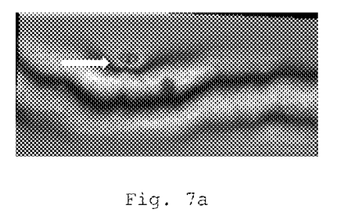
FIGS. 7a to 7d show interference images of a transparent sheet with a metallic inclusion, recorded at different detection angles.
Figure 7B:
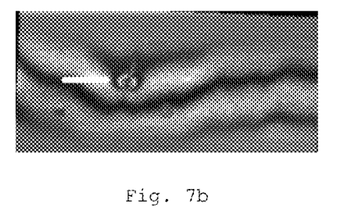
Figure 7C:
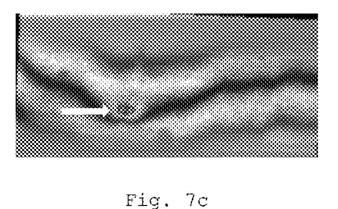
Figure 7D:
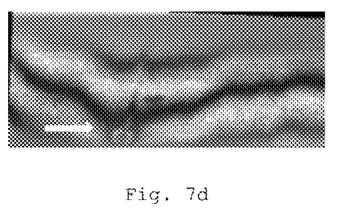

FIGS. 5, 6 show a comparison of interference images and microscopic images of glass sheets that have defects.

Each of FIGS. 5a, 5b shows a glass sheet with an inclusion having a size of 0.060×0.005 mm². Each of FIGS. 6a and 6b shows a glass sheet with a gas bubble having a size of 0.090×0.020 mm². FIGS. 5a, 6a are interference images. FIGS. 5b, 6b are bright field microscopic images at 100-fold magnification.

The interference effect caused by the defect is greater by many times (about 10 to 14 times greater) than the defect itself.

The defect is detected by comparing the interference images, the comparison comprising to determine differences between the interference images. In the present exemplary embodiment, interference images are used which have been produced at the same time.

FIGS. 7 and 8 show interference images of two glass sheets 10, or samples, each having a defect. The defects are as follows:
1) metallic inclusion having a core size of about 0.150 mm (FIGS. 7a to 7d); and
2) gas bubble having a size of 0.06 mm (FIGS. 8a to 8d).

Both samples 10 were inspected by an apparatus 11 according to FIG. 3. For each sample, four interference images were recorded at different illumination angles. The difference in the illumination angles between successive interference images is 1 to 2 degrees.

A comparison of FIGS. 7 and 8 shows that the interference pattern caused by the defect varies quickly relative to the basic interference pattern of sheet 10. The four images have different patterns which in total allow a more complex representation. The representation is useful for a subsequent pattern recognition.

Figure 8A:
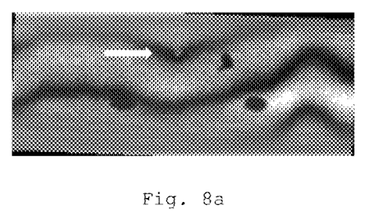
FIGS. 8a to 8d show interference images of a transparent sheet with a gas bubble, recorded at different detection angles.
Figure 8B:
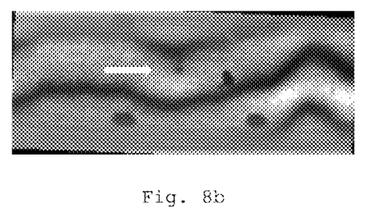
Figure 8C:
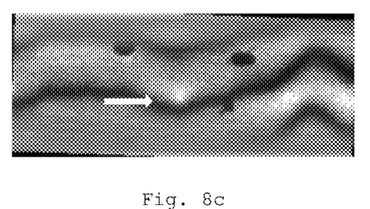
Figure 8D:
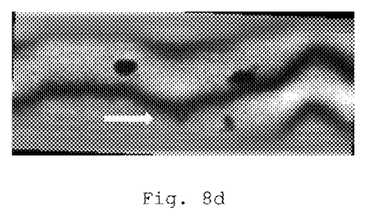

In case the defect is a glass bubble (FIGS. 8a to 8d), the defect would not be reliably distinguishable from the interference pattern of sheet 10 from only a single interference image according to FIG. 8c. In the interference image as shown in FIG. 8b, the defect is recognizable, but it is not distinguishable from a light absorbing contamination at the surface of sheet 10. However, a combination of interference images of FIGS. 8*a* and 8*d* allows to reliably identify the defect. Repeated observation is therefore very advantageous for detecting very small defects. Apparatus 11 enables to identify solid inclusions of a core size smaller than 0.05 mm and gas inclusions of a core size smaller than 0.150 mm.

In the manufacturing of thin glass (thickness from about 0.02 to 1 mm), high feeding rates are partly necessary because of the process, partly economically desirable. At the same time, high glass defect sensitivities are required, especially for very thin glasses. The invention permits to achieve high defect sensitivity at high feeding rates under manufacturing conditions (tolerance to variations in height, glass deflection) with reasonable effort.

For image analysis, a plurality of images ii>2 are captured for each position. Interference patterns caused by defects and impurities are small compared to the image field. The interference pattern of the undisturbed sheet material is created by a gradual change of the sheet thickness, in contrast to the interference pattern caused by defects. Therefore, an optical thickness can be determined from each image by smoothing, which is identical for all images ii.

Therefore, by forward calculation taking into account the changed capturing situation, an expectation interference pattern can be determined for the respective other interference images, which is subtracted from the actual image for all images ii. A defect will then be distinguished by the fact that it deviates from the expectation value in different images. This deviation between all images is added up, so that small defects can be identified and larger defects can be identified in more detail. Dirt and stain can be discriminated due to their consistent behavior in all images.

Defects in the glass will cause a local disturbance in the glass that depends on the defect type (bubble, inclusion, etc.) and the defect size relative to the glass thickness. The disturbance locally changes the optical wavelength of the light beam that passes through this region as compared to a light beam which passes through an undisturbed region. In an arrangement as shown in FIG. 2, this effect may be observed on screen 14.

When using a light source 12 with a sufficient coherence length, the light beams 22*a*, 22*b* reflected at the upper and lower surfaces will interfere. Due to the high homogeneity of the glass (in terms of variations in thickness and variations in refractive index), the path difference of the interfering partial beams changes only "slowly" when compared to a region in the vicinity of a defect. Here, the striped pattern will exhibit a disturbance which can be observed by an image sensor 16 focused on screen 14.

The invention has a variety of advantages.

The local disturbance is greater by many times than the actual defect, usually by 10 to 12 times. Thus, a lower optical resolution is necessary, with a positive impact on the cost and the achievable depth of field. However, the resolution should be sufficient to resolve a light/dark/light or complementary pattern.

The disturbance is caused by glass defects. Dust/dirt on the surface do not produce any interference effect, so that glass defects can be distinguished from dust.

The method employs reflected light instead of transmitted light, so that no interruption of the conveyor is necessary in case of continuous material, which in turn simplifies the configuration.

By guiding a flexible glass ribbon 10 over a roller 25, the position relative to illumination means 12 and camera 16 is fixed in a simple manner. Moreover, the tension imposed by the bending compensates for warpage caused by local stresses in the glass ribbon.

The method is insensitive to variations in height. The angle tolerance required can be accommodated by beam expansion or by employing area scan cameras. Apparatus 11 initially uses only one channel, and in conjunction with the lower resolution it is suitable for high feeding rates.

By using a further wavelength which inverts the pattern, a further information is resulting for each glass defect, so that smaller defects would be found or a lower resolution is needed for the same defect sensitivity.

In summary, the apparatus 11 of the invention provides for a simple and cost efficient configuration with a very high performance in terms of detection of defects, in particular small defects.

REFERENCE NUMERALS

10 Transparent sheet, glass ribbon, test object, sample
11 Apparatus for identifying a defect within the volume of a transparent sheet
12 Illumination means, light source
14 Screen
16 Image sensor, sensor line, camera
18 Computing unit
20 Incident light
22 Light backscattered or reflected from the sheet
22*a* Light reflected from the upper surface of the sheet
22*b* Light reflected from the lower surface of the sheet
24 Conveyor means
25 Roller
26 Beam splitter

What is claimed is:

1. An apparatus for identifying defects within the volume of a transparent sheet, comprising:
    an illumination device that directs incident light onto at least a portion of a surface of the sheet to illuminate the sheet; and
    an image detector onto which the incident light that is backscattered from the sheet is directed,
    wherein the apparatus is adapted to generate interference patterns by superposition of components of the light backscattered from the sheet and, based on interference patterns, to generate at least two interference images under different capturing conditions in order to identify the defects by evaluating the at least two interference images.

2. The apparatus as claimed in claim 1, wherein the image detector generates the at least two interference images in order to identify the defects by comparing the at least two interference images.

3. The apparatus as claimed in claim 1, wherein the image detector generates the at least two interference images in order to identify the defects by determining differences between the at least two interference images.

4. The apparatus as claimed in claim 1, wherein the image detector generates the at least two interference images sequentially in time.

5. The apparatus as claimed in claim 1, wherein the image detector generates the at least two interference images at the same time.

6. The apparatus as claimed in claim 1, wherein the different capturing conditions are selected from the group consisting of incident light of at least two different wavelengths, incident light of least two different waveforms, incident light directed onto the sheet at least two different angles of illumination, capture of the backscattered light at least two different detection angles, incident light of at least two different phases, and any combination thereof.

7. The apparatus as claimed in claim 1, wherein the illumination device comprises at least one light source in form of a sodium vapor lamp or a laser.

8. The apparatus as claimed in claim 7, wherein the at least one light source has a coherence length greater than twice a thickness of the sheet.

9. The apparatus as claimed in claim 7, wherein the at least one light source has a coherence length greater than 3 mm.

10. The apparatus as claimed in claim 1, wherein the image detector comprises a screen onto which the backscattered light from the sheet is directed for displaying the interference images.

11. The apparatus as claimed in claim 1, wherein the image detector comprises at least one image sensor for capturing the backscattered light from the sheet.

12. The apparatus as claimed in claim 11, wherein the at least one image sensor is selected from the group consisting of a matrix camera, a line scan camera, a line scan camera with Time Delayed Integration (TDI) sensor, which is operated as a matrix camera, and combinations thereof.

13. The apparatus as claimed in claim 11, wherein the image detector further comprises a screen onto which the interference images captured by the image sensor are displayed.

14. The apparatus as claimed in claim 1, further comprising a computer connected to the image detector and/or to the illumination device.

15. The apparatus as claimed in claim 1, further comprising a conveyor for moving the sheet relative to the illumination device and/or the image detector.

16. The apparatus as claimed in claim 15, wherein the conveyor comprises a roller over which the sheet is guided.

17. The apparatus as claimed in claim 1, further comprising a pattern recognition system for evaluating the at least two interference images.

18. The apparatus as claimed in claim 1, wherein the illumination device comprises a device selected from the group consisting of a tunable light source for generating the incident light with a plurality of different wavelengths sequentially in time, a light source having a defined spectral width and a tunable filter for generating the incident light with a plurality of different wavelengths sequentially in time, a plurality of spaced apart light sources for simultaneously generating the incident light of a plurality of different wavelengths, and combinations thereof.

19. A method for identifying defects within the volume of a transparent sheet, comprising:
    generating and directing incident light onto at least a portion of a surface of the sheet;
    directing light backscattered from the sheet onto an image detector, so that components of the light backscattered from the sheet are superposed to generate interference patterns;
    capturing light backscattered from the sheet with the image detector;
    generating by means of the interference patterns at least two interference images at the image detector under different capturing conditions; and
    identifying the defects by evaluating the at least two interference images.

20. The method as claimed in claim 19, wherein identifying the defects comprises comparing the at least two interference images with one another.

* * * * *